United States Patent [19]
Lange et al.

[11] Patent Number: 6,036,682
[45] Date of Patent: *Mar. 14, 2000

[54] CATHETER HAVING A PLURALITY OF INTEGRAL RADIOPAQUE BANDS

[75] Inventors: Michael R. Lange, St. Paul; Martin R. Willard, Maple Grove, both of Minn.

[73] Assignee: SciMed Life Systems, Inc., Maple Grove, Minn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/982,538

[22] Filed: Dec. 2, 1997

[51] Int. Cl.⁷ .............................. A61M 25/00; A61M 5/00
[52] U.S. Cl. ............................................ 604/529; 604/264
[58] Field of Search ...................... 604/264, 280, 604/93, 915, 529; 600/435, 434, 433

[56] References Cited

U.S. PATENT DOCUMENTS

| | | | |
|---|---|---|---|
| 2,212,334 | 8/1940 | Wallerich | 264/330 |
| 2,810,424 | 10/1957 | Swartswelter et al. | 154/1.8 |
| 2,857,915 | 10/1958 | Sheridan | 128/349 |
| 2,934,514 | 1/1960 | Salyer et al. | 260/15.5 |
| 3,070,132 | 12/1962 | Sheridan | 138/118 |
| 3,336,918 | 8/1967 | Jeckel | 128/2.05 |
| 3,416,531 | 12/1968 | Edwards | 128/354 |
| 3,485,234 | 12/1969 | Stevens | 128/2 |
| 3,529,633 | 9/1970 | Vaillancourt | 138/118 |
| 3,561,493 | 2/1971 | Maillard et al. | |
| 3,605,750 | 9/1971 | Sheridan et al. | 128/348 |
| 3,608,555 | 9/1971 | Greyson | 128/348 |
| 3,612,058 | 10/1971 | Ackerman | 128/348 |
| 3,618,614 | 11/1971 | Flynn | 128/348 |

(List continued on next page.)

FOREIGN PATENT DOCUMENTS

| | | |
|---|---|---|
| 0 277 366 A1 | 8/1988 | European Pat. Off. |
| 0 399 799 B1 | 11/1989 | European Pat. Off. |
| 0 473 045 | 8/1990 | European Pat. Off. |
| 0 439 932 B1 | 8/1991 | European Pat. Off. |
| 0 180 348 B1 | 5/1992 | European Pat. Off. |
| 0 555 088 A2 | 8/1993 | European Pat. Off. |
| 0 555 088 A3 | 8/1993 | European Pat. Off. |
| WO 92/15356 | 9/1992 | WIPO |
| WO 96/26758 | 9/1996 | WIPO |

OTHER PUBLICATIONS

Johnson, "Paste Extrusion of Filled TFE–Fluorocarbon Resin for Wire Insulations", Technical Papers vol. VII, Seventeenth Annual Technical Conference of Society of Plastics Engineers, Inc., Washington, D.C. Jan. 1961.

*Encyclopedia of Polymer Science and Technology*, vol. 13, John Wiley & Sons, Inc., Copyright 1970, pp.1 623–654.

*Fluoropolymers, Organic*, vol. A11, Veragsgesellschaft mbH, Germany, Copyright 1988, pp. 393–428.

Lonz et al., "Extrusion Properties of Lubricated Resin from Coagulated Dispersion", *Industrial and Engineering Chemistry*, vol. 44, No. 8, Aug. 1952, pp. 1805–1810.

Kolobow et al., "A new thin–walled nonkinking catheter for peripheral vascular cannulation", Surgery, vol. 68, No. 4, Oct., 1970, pp. 625–626.

*Primary Examiner*—Corrine McDermott
*Assistant Examiner*—Michael J. Hayes
*Attorney, Agent, or Firm*—Crompton, Seager & Tufte, LLC

[57] ABSTRACT

A tubular member for manufacture of medical devices insertable into body lumens. The tubular member includes an inner tubular member, and outer tubular member, and a lumen through the inner tubular member. The outer tubular member has a plurality of radiopaque segments formed of radiopaque material incorporated into the tube polymeric material. One tubular member has highly radiopaque segments separated by less radiopaque segments at intervals greater than the radiopaque segment length, such that the radiopaque segments serve as marker bands. Another tubular member has long radiopaque segments separated by less radiopaque segments at intervals less than the radiopaque segment length, such that the less radiopaque segments serve as marker bands. Marker bands can be located at either regular intervals to aid in measuring internal dimensions or at significant structural locations to aid in catheter positioning.

14 Claims, 4 Drawing Sheets

U.S. PATENT DOCUMENTS

| | | | |
|---|---|---|---|
| 3,888,249 | 6/1975 | Spencer | 128/214 R |
| 3,911,927 | 10/1975 | Rich et al. | 128/349 R |
| 3,924,632 | 12/1975 | Cook | 128/348 |
| 3,962,153 | 6/1976 | Gore | 260/2.5 R |
| 4,027,659 | 6/1977 | Slingluff | 128/2 M |
| 4,066,743 | 1/1978 | Kneller | 424/5 |
| 4,125,599 | 11/1978 | Wiegert | 424/5 |
| 4,160,015 | 7/1979 | Wiegert | 424/5 |
| 4,182,787 | 1/1980 | Goosens et al. | 428/36 |
| 4,191,185 | 3/1980 | Lemieux | 128/214.4 |
| 4,210,478 | 7/1980 | Shoney | 156/242 |
| 4,211,741 | 7/1980 | Ostoich | 264/173 |
| 4,250,072 | 2/1981 | Flynn | 260/31.2 N |
| 4,277,432 | 7/1981 | Woinowski | 264/173 |
| 4,279,252 | 7/1981 | Martin | 128/349 R |
| 4,282,876 | 8/1981 | Flynn | 128/349 R |
| 4,283,447 | 8/1981 | Flynn | 428/36 |
| 4,306,562 | 12/1981 | Osborne | 128/348 |
| 4,318,402 | 3/1982 | Vaillancourt | 128/214.4 |
| 4,321,226 | 3/1982 | Markling | 264/139 |
| 4,385,635 | 5/1983 | Ruiz | 128/658 |
| 4,402,684 | 9/1983 | Jessup | 604/264 |
| 4,419,095 | 12/1983 | Nebergall et al. | 604/96 |
| 4,425,919 | 1/1984 | Alston, Jr. et al. | 128/658 |
| 4,430,082 | 2/1984 | Schwabacher | 604/263 |
| 4,430,083 | 2/1984 | Ganz et al. | 604/283 |
| 4,469,483 | 9/1984 | Becker et al. | 604/280 |
| 4,516,970 | 5/1985 | Kaufman et al. | 604/270 |
| 4,516,972 | 5/1985 | Samson | 604/282 |
| 4,531,943 | 7/1985 | Van Tassel et al. | 604/280 |
| 4,563,181 | 1/1986 | Wijayarathna et al. | 604/280 |
| 4,568,338 | 2/1986 | Todd | 604/281 |
| 4,577,543 | 3/1986 | Wilson | 87/11 |
| 4,588,399 | 5/1986 | Nebergall et al. | 604/280 |
| 4,596,563 | 6/1986 | Pande | 604/264 |
| 4,636,346 | 1/1987 | Gold et al. | 264/139 |
| 4,657,024 | 4/1987 | Coneys | 128/658 |
| 4,661,094 | 4/1987 | Simpson | 604/53 |
| 4,662,404 | 5/1987 | LeVeen et al. | 138/120 |
| 4,665,604 | 5/1987 | Dubowik | 29/415 |
| 4,690,175 | 9/1987 | Ouchi et al. | 138/131 |
| 4,705,511 | 11/1987 | Kocak | 604/282 |
| 4,735,602 | 4/1988 | Ruiz | 604/281 |
| 4,739,768 | 4/1988 | Engelson | 128/658 |
| 4,764,324 | 8/1988 | Burnham | 264/103 |
| 4,784,638 | 11/1988 | Ghajar et al. | 604/49 |
| 4,806,182 | 2/1989 | Rydell et al. | 156/211 |
| 4,817,613 | 4/1989 | Jaraczewski et al. | 128/658 |
| 4,838,879 | 6/1989 | Tanabe et al. | 604/280 |
| 4,842,590 | 6/1989 | Tanabe et al. | 604/282 |
| 4,863,442 | 9/1989 | Demello et al. | 604/282 |
| 4,886,506 | 12/1989 | Lovgren et al. | 604/280 |
| 4,898,591 | 2/1990 | Jang et al. | 604/282 |
| 4,899,787 | 2/1990 | Ouchi et al. | 138/131 |
| 4,925,710 | 5/1990 | Buck et al. | 428/34.5 |
| 4,935,017 | 6/1990 | Sylvanowicz | 604/280 |
| 4,961,731 | 10/1990 | Bodicky et al. | 604/264 |
| 4,963,306 | 10/1990 | Weldon | 264/101 |
| 4,968,307 | 11/1990 | Dake et al. | 604/264 |
| 5,017,259 | 5/1991 | Kohsai | 156/294 |
| 5,019,057 | 5/1991 | Truckai | 604/282 |
| 5,021,044 | 6/1991 | Sharkawy | 604/53 |
| 5,037,403 | 8/1991 | Garciaq | 604/280 |
| 5,045,072 | 9/1991 | Castillo et al. | 604/280 |
| 5,057,092 | 10/1991 | Webster, Jr. | 604/282 |
| 5,061,257 | 10/1991 | Martinez et al. | 604/282 |
| 5,069,673 | 12/1991 | Shwab | 604/280 |
| 5,069,674 | 12/1991 | Fearnot et al. | 604/282 |
| 5,078,702 | 1/1992 | Pomeranz | 604/280 |
| 5,088,991 | 2/1992 | Weldon | 604/280 |
| 5,120,323 | 6/1992 | Shockey et al. | 604/282 |
| 5,160,559 | 11/1992 | Scovil et al. | 156/73.6 |
| 5,171,232 | 12/1992 | Castillo et al. | 604/280 |
| 5,176,660 | 1/1993 | Truckai | 604/282 |
| 5,190,520 | 3/1993 | Fenton, Jr. et al. | 604/43 |
| 5,199,950 | 4/1993 | Schmitt et al. | 604/95 |
| 5,201,723 | 4/1993 | Quinn | 604/264 |
| 5,217,440 | 6/1993 | Frassica | 604/282 |
| 5,221,270 | 6/1993 | Parker | 604/282 |
| 5,221,372 | 6/1993 | Olson | 148/326 |
| 5,222,949 | 6/1993 | Kaldany | 604/282 |
| 5,234,416 | 8/1993 | Macaalay et al. | 604/282 |
| 5,254,107 | 10/1993 | Soltesz | 604/282 |
| 5,256,158 | 10/1993 | Tolkoff et al. | 604/280 |
| 5,267,982 | 12/1993 | Sylvanowicz | 604/281 |
| 5,279,596 | 1/1994 | Castaneda et al. | 604/282 |
| 5,290,229 | 3/1994 | Paskar | 604/95 |
| 5,300,048 | 4/1994 | Drewes, Jr. et al. | 604/280 |
| 5,306,252 | 4/1994 | Yuteri et al. | 604/164 |
| 5,306,263 | 4/1994 | Voda | 604/281 |
| 5,308,342 | 5/1994 | Sepetka | 604/282 |
| 5,318,032 | 6/1994 | Lonsbury et al. | 128/658 |
| 5,335,410 | 8/1994 | Burnham | 29/452 |
| 5,358,493 | 10/1994 | Schweich, Jr. et al. | 604/264 |
| 5,389,090 | 2/1995 | Fischell et al. | 604/280 |
| 5,399,164 | 3/1995 | Snoke et al. | 604/95 |
| 5,401,258 | 3/1995 | Voda | 604/281 |
| 5,403,292 | 4/1995 | Ju | 604/282 |
| 5,425,723 | 6/1995 | Wang | 604/280 |
| 5,433,713 | 7/1995 | Trotta | 604/264 |
| 5,441,489 | 8/1995 | Utsumi et al. | 604/280 |
| 5,445,624 | 8/1995 | Jimenez | 604/280 |
| 5,445,625 | 8/1995 | Voda | 604/281 |
| 5,472,435 | 12/1995 | Sutton | 604/282 |
| 5,489,277 | 2/1996 | Tolkoff | 604/280 |
| 5,498,250 | 3/1996 | Prather | 604/280 |
| 5,509,910 | 4/1996 | Lunn | 604/282 |
| 5,514,236 | 5/1996 | Avellanet et al. | 156/154 |
| 5,531,721 | 7/1996 | Pepin et al. | 604/282 |
| 5,533,985 | 7/1996 | Wang | 604/264 |
| 5,538,512 | 7/1996 | Zenzon et al. | 604/280 |
| 5,538,513 | 7/1996 | Okajima | 604/282 |
| 5,542,924 | 8/1996 | Snoke et al. | 604/95 |
| 5,542,937 | 8/1996 | Chee et al. | 604/280 |
| 5,545,149 | 8/1996 | Brin et al. | 604/265 |
| 5,545,151 | 8/1996 | O'Connor et al. | 604/282 |
| 5,554,139 | 9/1996 | Skoajima | 604/282 |
| 5,569,200 | 10/1996 | Umeno et al. | 604/96 |
| 5,569,218 | 10/1996 | Berg | 604/282 |
| 5,584,821 | 12/1996 | Hobbs et al. | 604/280 |
| 5,599,319 | 2/1997 | Stevens | 604/264 |
| 5,599,325 | 2/1997 | Ju et al. | 604/282 |
| 5,599,326 | 2/1997 | Carter | 604/282 |
| 5,603,705 | 2/1997 | Berg | 604/282 |
| 5,614,136 | 3/1997 | Pepin et al. | 264/40.3 |
| 5,634,897 | 6/1997 | Dance et al. | 604/35 |
| 5,658,263 | 8/1997 | Dang et al. | 604/280 |
| 5,662,621 | 9/1997 | Lafontaine | 604/281 |
| 5,662,622 | 9/1997 | Gore et al. | 604/282 |
| 5,666,969 | 9/1997 | Urick et al. | 128/772 |
| 5,674,208 | 10/1997 | Berg et al. | 604/282 |
| 5,676,659 | 10/1997 | McGurk | 604/282 |
| 5,680,873 | 10/1997 | Berg et al. | 128/772 |
| 5,695,483 | 12/1997 | Samson | 604/282 |

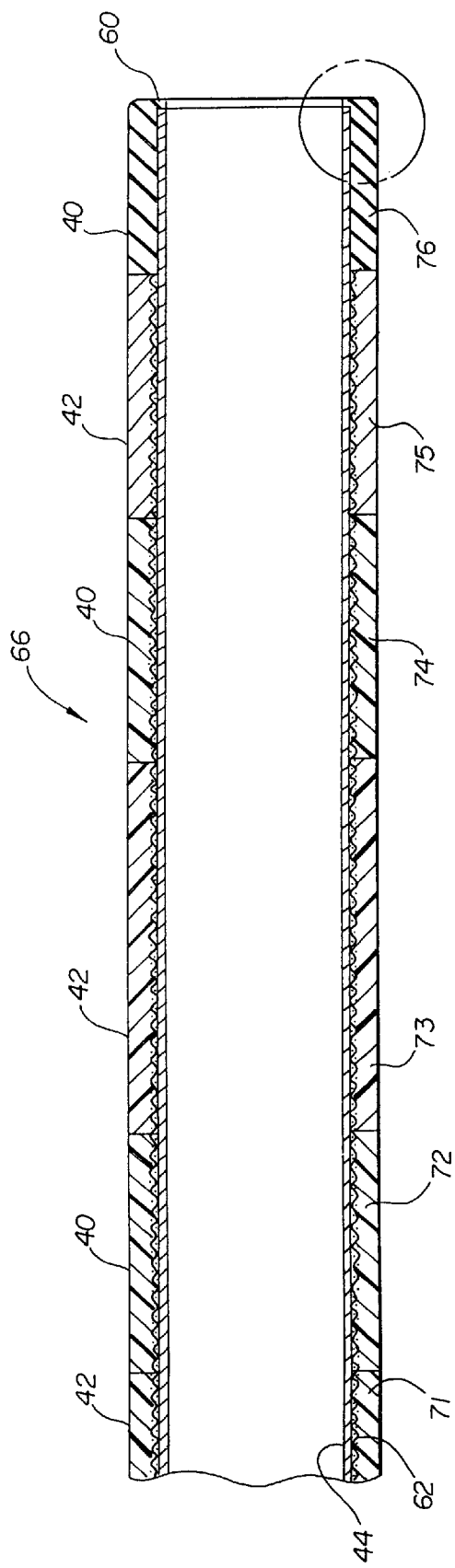
Fig. 8
Fig. 9
Fig. 10

CATHETER HAVING A PLURALITY OF INTEGRAL RADIOPAQUE BANDS

CROSS-REFERENCE TO RELATED APPLICATIONS

The present application is related to U.S. patent application Ser. No. 08/800,927, now U.S. Pat. No. 5,911,715, filed on Feb. 13, 1997, entitled GUIDE CATHETER HAVING SELECTED FLEXURAL MODULUS SEGMENTS, herein incorporated by reference.

FIELD OF THE INVENTION

The present invention generally relates to the field of tubular medical devices insertable into body lumens, and more specifically refers to the field of catheters having radiopaque portions rendering the catheters visible under fluoroscopy. In particular, the present invention relates to an improved catheter having highly radiopaque regions separated by less radiopaque regions, wherein the radiopacity is provided by radiopaque material incorporated into a polymeric material within the catheter.

BACKGROUND OF THE INVENTION

Tubular medical devices insertable into body lumens are well known in the medical field. Catheters are used diagnostically to inject contrast media, measure internal body dimensions, retrieve biopsy samples, and optically inspect internal body sites. Catheters are used therapeutically to deliver drugs, drain fluids, retrieve stones, deliver ultrasound, deliver laser light, provide access for minimally invasive surgery instruments and dilatate narrowed vessel passages. Intravascular catheters for the treatment of cardiovascular disease have become particularly well known in the field of medicine.

Other tubular devices are used in conjunction with diagnostic and therapeutic catheters. Guide wires provide an established path to and from target sites, allowing rapid advancement and retraction of catheters over the guide wires. Guide catheters provide a lubricous conduit within which other catheters can be introduced into the body.

Introducing catheters into the body often requires fluoroscopic visualization to aid the treating physician in guiding the catheter to the target site. In particular, intravascular cardiac guide catheters are often inserted into the femoral artery near the groin, advanced over the aortic arch, advanced into a coronary artery ostium, and further advanced to a coronary artery site of interest. In particular, inserting the guide catheter distal end into a coronary artery ostium requires an accurate image of the location and orientation of the catheter. Catheters are commonly formed of a non-radiopaque polymeric material. Therefore, a metallic radiopaque marker band is often added to the catheter distal end to render this region of the catheter visible under fluoroscopy. Platinum and gold are two commonly used maker band metals.

Marker bands can present problems. In particular, metallic marker bands require fixation to the underlying catheter, to avoid slippage as the catheter is advanced or retracted. The fixation of metallic marker bands to small diameter catheters adds complexity to the manufacturing process. The bands can protrude from the tube surface, presenting an undesirable increased profile. The bands can also provide a decrease in lubricity and an increase in stiffness in the local area of the band. The use of metallic bands as radiopaque markers has restricted their use to limited areas for the foregoing reasons.

What would be desirable and has not heretofore been provided is a tubular medical device having radiopaque markers disposed integrally with the tubular body. A tubular device being radiopaque or having radiopaque marker bands over most of the tubular body would be desirable. Radiopaque marker bands not having surface protrusions or the possibility of band slippage would be desirable.

SUMMARY OF THE INVENTION

The present invention includes radiopaquely marked tubular members for medical devices insertable into body lumens. Medical devices suitable for incorporating the present invention include guide catheters, therapeutic catheters, diagnostic catheters, and polymerically coated guide wires. A preferred group of devices for utilizing the present invention is intravascular guide catheters.

The present invention includes a plurality of highly radiopaque, annular tubular segments separated by less radiopaque segments. The highly radiopaque segments are formed of polymeric material having highly radiopaque material incorporated therein, thereby forming radiopaque segments that are substantially homogeneous and integral with the abutting, less radiopaque segments. A preferred polymeric material is polyether block amide. Preferred radiopaque materials include barium sulfate, bismuth subcarbonate and tungsten. The radiopaque material is preferably finely ground and dispersed with the polymeric resin prior to extrusion.

In one tubular member, the highly radiopaque segments have a length that is substantially less than the length of the less radiopaque segments separating the highly radiopaque segments. In this embodiment, the marker bands are formed of the highly radiopaque segments. In another tubular member, the highly radiopaque segment length is substantially greater than the length of the less radiopaque segments separating the highly radioactive segments. In this embodiment, the marker bands are effectively formed of the less radiopaque segments.

In one embodiment, the marker bands are separated by substantially equal distances along the length of the tubular member. This embodiment is suitable for use as a marking or measuring catheter. In another embodiment, the marker bands are positioned near structurally significant locations along the catheter. In one embodiment, the marker bands are positioned at the distal end, primary curve, and secondary curve.

A preferred method for making the tubular members includes extruding a lubricous inner tubular member and forming a support member about the inner tubular member. A preferred support member is formed by wrapping stainless steel wire about the inner tubular member, thereby forming a wire braid. Outer tubular members are preferably formed by extruding a suitable polymer such as polyether block amide, available as PEBAX. Highly radiopaque outer tubes can be formed by mixing radiopaque material with the resin, followed by extrusion. Less radiopaque outer tubes are formed in a similar manner, but without the added radiopaque material.

The outer tubular members can be cut to desired lengths and slipped over the braid covered inner tubular member such that the various outer tubes segments abut each other. Highly radiopaque segments are formed from highly radiopaque outer tubes and less radiopaque segments are formed from the less radiopaque tubes. After covering the inner tube with outer tube segments, a forming sleeve can be disposed over the outer tubular segments and heat applied. The heat at least partially melts the outer tube segments, fusing the abutting ends and bonding the outer tubes to the inner tube. The sleeve can then be removed, leaving a tube having highly radiopaque segments joined to less radiopaque segments.

BRIEF DESCRIPTION OF THE DRAWINGS

The invention will be further described with reference to the accompanying drawings where like numbers refer to like parts in several views and wherein:

FIG. 8 is a partial, longitudinal cross-sectional view of a distal portion of a catheter tube or guide catheter depicting a preferred distal construction;

FIG. 9 is a detailed, partial, cross-sectional view of the tip region indicated in FIG. 8 showing a preferred tip construction; and FIG. 10 is a detailed, partial, cross-sectional view of an alternative embodiment of the tip configuration of FIG. 9, depicting the inner tubular member extending to the distal end of the catheter tube.

DETAILED DESCRIPTION OF THE PREFERRED EMBODIMENTS

Figure 1:
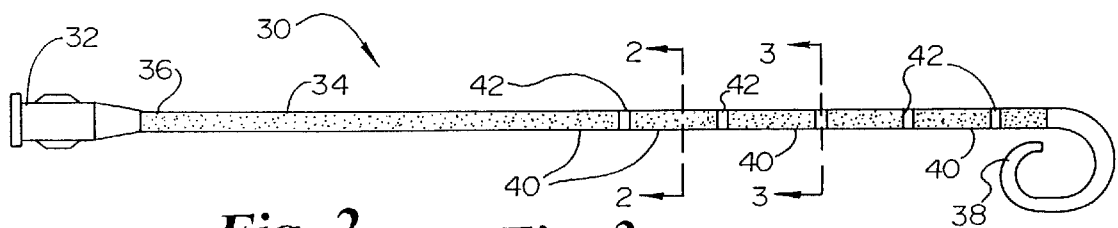
FIG. 1 is a plan view of a guide catheter having longer, highly radiopaque segments separated by shorter, less radiopaque segments, such that the catheter is visible under fluoroscopy and the less radiopaque segments serve as marker bands.

FIG. 1 illustrates a tubular guide catheter 30 having a hub 32, a shaft 34, a proximal end 36, and a distal end 38. Shaft 34 has a plurality of highly radiopaque segments 40 separated by less radiopaque segments 42. In the embodiment illustrated, highly radiopaque segments 40 have lengths, on average, substantially longer than the length of the tubular segment or interval separating the highly radiopaque segments. Separating highly radiopaque segments 40 are less radiopaque segments 42.

A substantial portion of the length of the shaft 34 in FIG. 1 is formed of highly radiopaque segments, such that a majority of the length of shaft 34 is highly radiopaque, with the less radiopaque segments effectively serving as marker bands. This provides an advantage over catheters having a catheter substantially invisible under fluoroscopy, but for limited radiopaque marker bands. A substantial portion of catheter 30 is visible under fluoroscopy, which can aid in positioning the catheter.

In the embodiment of FIG. 1, less radiopaque segments 42 are separated by substantially equally distances. Catheter 30 can serve as a measuring or marking catheter to allow the measurement of cardiac and vascular distances under fluoroscopy. The use of marking catheters is described in U.S. Pat. No. 4,279,252, issued to Martin, herein incorporated by reference.

Figure 2:
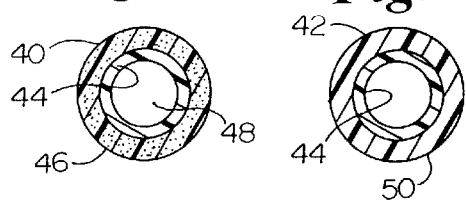
FIG. 2 is a transverse, cross-sectional view of FIG. 1 along line 2—2, illustrating a highly radiopaque segment.

Referring now to FIG. 2, a transverse cross section through highly radiopaque segment 40 is illustrated, having an inner tube 44, and outer, highly radiopaque tube 46, and a lumen 48 extending therethrough. Inner tube 44 is preferably formed of a lubricous material, as the lubricity eases the passage of catheters through guide catheter 30. In a preferred embodiment, inner tube 44 is formed of polytetrafluoroethylene (PTFE). Outer radiopaque tube 46 can vary in composition over the length of catheter 30, for example, imparting specific degrees of flexibility at specific locations. In one embodiment, outer radiopaque tube 46 is formed of polyether block amide, such as PEBAX. The degree of cross linking of the PEBAX can be selected to vary the stiffness as desired, selecting a higher degree of cross linking to obtain stiffer polymer.

Outer radiopaque tube 46 is radiopaque primarily due to incorporation of highly radiopaque material within the tubular material forming the tube. In a preferred embodiment, outer radiopaque tube is formed of PEBAX and has finely ground particles of radiopaque material embedded within the polymer. Preferred radiopaque materials include barium sulfate, bismuth subcarbonate, bismuth trioxide, and tungsten. Radiopaque materials are preferably loaded within the polymer as high as possible without compromising the integrity of the polymeric tube. Radiopaque loading ranges from about 40% to about 75% in one set of embodiments. In one method, the radiopaque material is mixed with polymeric resin prior to mixing and extrusion.

As illustrated in FIG. 2, highly radiopaque segment 40 requires no metallic marker bands to render portions of catheter 30 fluoroscopically visible. Furthermore, making most of the catheter length highly radiopaque using metallic marker bands would compromise the flexibility of the catheter. Catheters having additional metallic marker bands increase manufacturing complexity and require means for insuring the metallic bands are fixed in place. Metallic bands also generally protrude from the tube surface and can provide frictional resistance to translational movement of the catheter.

Figure 3:
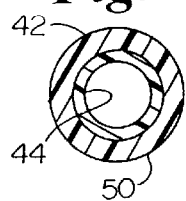
FIG. 3 is a transverse, cross-sectional view of FIG. 1 along line 3—3, illustrating a less radiopaque segment.

Referring now to FIG. 3, less radiopaque segment 42 is illustrated in cross section, having inner tube 44 disposed within less radiopaque tube 50. In one embodiment, less radiopaque outer tube 50 is formed of the same material as highly radiopaque outer tube 46, but with no highly radiopaque material incorporated within. In another embodiment, less radiopaque outer tube 50 has a different composition than highly radiopaque outer tube 46 to compensate for the material properties changed by high loading of radiopaque material.

In one method of manufacture, catheter 30 is formed from inner tube 44 initially completely surrounded by outer tube 46. Outer tube 46 can be coextruded over inner tube 44 to form the initial tubing. Segments of radiopaque outer tube 46 can be removed through grinding, leaving a band ground down part or all of the way to inner tube 44. The band can then be filled with polymeric material containing no radiopaque material. Suitable methods for filling the band include the use of molten polymer or adhesive in conjunction with processing sleeves.

Figure 4:
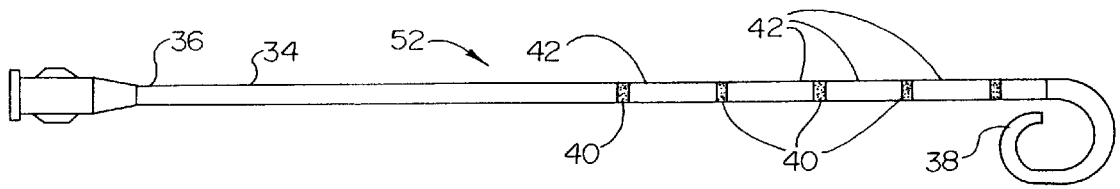
FIG. 4 is a plan view of a guide catheter having longer, less radiopaque segments separated by shorter, highly radiopaque segments, such that the highly radiopaque segments serve as marker bands.

Referring now to FIG. 4, another guide catheter 52 is illustrated, including shaft 34 having a plurality of shorter, highly radiopaque segments 40, and a plurality of longer, less radiopaque segments 42. Catheter 52 has a majority of its length formed of less radiopaque material, with highly radiopaque segments 40 serving as marker bands. Highly radiopaque segments 40 have lengths on average substantially shorter than the intervals separating the segments. Catheter 52 has highly radiopaque segments 40 separated at substantially equal intervals, allowing the catheter to serve as a measuring or marking catheter, as previously described. Catheter 52 can be manufactured in a similar manner to catheter 30, but with the less radiopaque outer tube segments corresponding to the highly radiopaque segments removed and refilled with highly radiopaque material.

Figure 5:
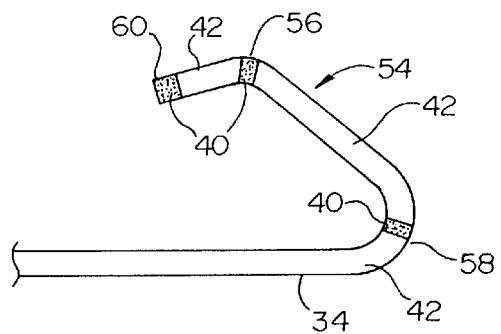
FIG. 5 is a partial plan view of a guide catheter having highly radiopaque segments marking structurally significant locations on the catheter.

Referring now to FIG. 5, another guide catheter 54 according to the present invention is illustrated. Catheter 54 illustrates an embodiment utilizing highly radiopaque segments 40 to mark structurally significant catheter locations. Guide catheter 54 includes a distal tip 60, a primary curve 56, and a secondary curve 58. Distal tip 60, primary curve 56, and secondary curve 58 are important structural features of catheter 54. In use, primary curve 56 bends catheter 54, orienting distal tip 60 towards a coronary artery ostium, allowing the treating physician to insert distal tip 60 into the coronary artery. In use, secondary curve 58 bends catheter 54, providing support for maintaining the position of distal tip 60 within a coronary artery ostium. In some embodiments, at least a portion of secondary curve 58, primary curve 56, and the shaft portion therebetween lies against the wall of the aorta opposite the coronary artery ostium being treated. Guide catheter shapes, structurally significant catheter portions, primary curves and secondary curves are discussed in more detail in U.S. Pat. No. 5,445,625, issued to Voda, herein incorporated by reference. Catheter 54 allows the treating physician to obtain fluoroscopic visual feedback on the location of the structurally significant catheter locations.

Figure 6:
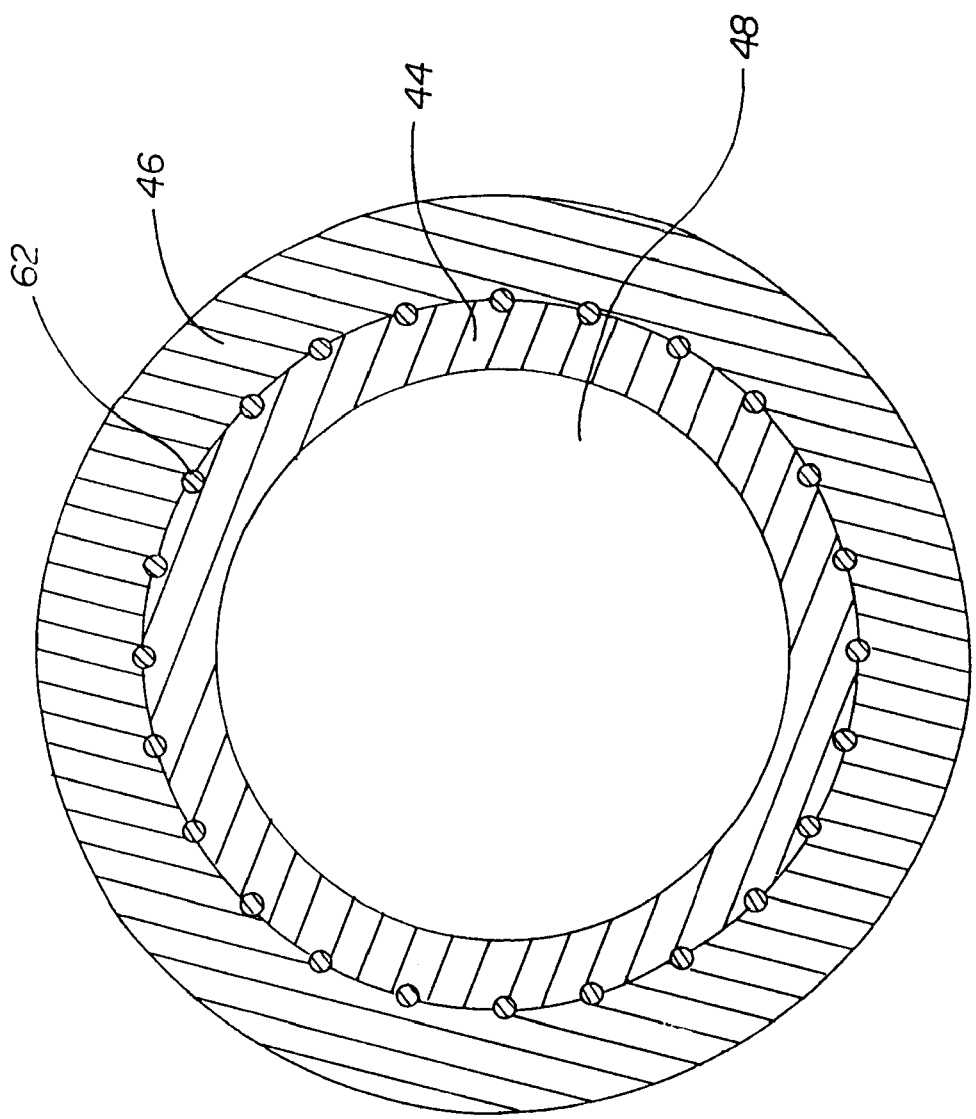
FIG. 6 is a cross-sectional view of FIG. 4 along line 6—6, illustrating inner tube, support member, and outer tube.

Referring now to FIG. 6, a transverse cross section of guide catheter 52 of FIG. 4 is illustrated, having outer, highly radiopaque tube 46, inner tube 44, lumen 48 and a support member 62. In a preferred embodiment, support member 62 is a stainless steel braid. In another embodiment, support member 62 is formed from stiff, polymeric strands. Support member 62 can provide improved torqueability to the catheter shaft.

Figure 7:
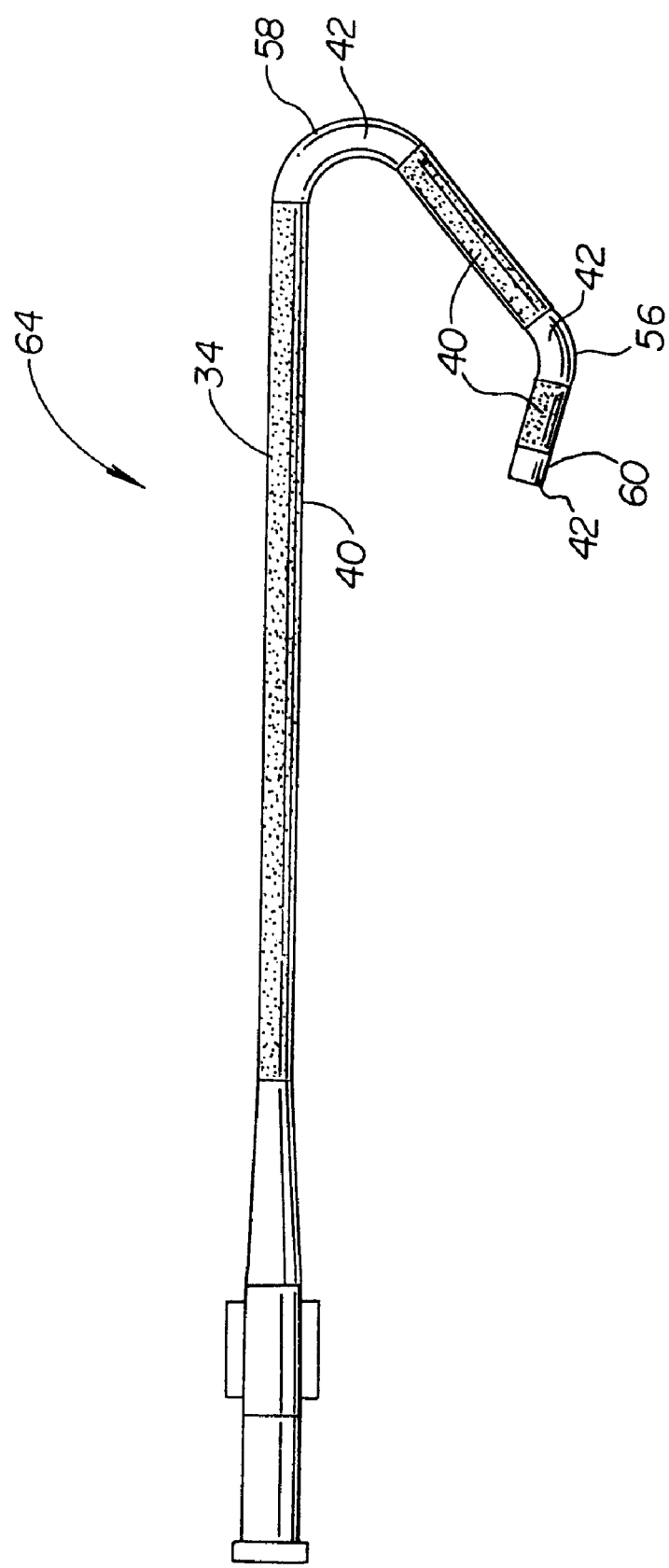
FIG. 7 is a plan view of a guide catheter having less radiopaque segments marking structurally significant locations.

Referring now to FIG. 7, another guide catheter 64 embodying the present invention is illustrated. Catheter 64 is similar to catheter 54 of FIG. 5 in being marked at structurally significant locations. Catheter 64 is marked using less radiopaque segments as illustrated in FIG. 1 rather than highly radiopaque segments as illustrated in FIG. 2. Less radiopaque segments 42 mark distal tip 60, primary curve 56, and secondary curve 58. Making distal tip 60 less radiopaque provides improved visibility of the ostium when inserting the tip, while still allowing the tip to be located under fluoroscopy, due to the proximally adjacent highly radiopaque segment. A majority of the length of catheter 64 is radiopaque, making most the catheter visible under fluoroscopy, allowing the treating physician to see the placement of the catheter body, the placement of structurally significant locations, and movement of the catheter through movement of the less radiopaque bands while the catheter is being maneuvered through the vasculature.

Referring now to FIG. 8, a catheter shaft distal section 66 is illustrated, having a series of alternating highly radiopaque segments 40 and less radiopaque segments 42. Section 66 incorporates a plurality of discrete, outer tubular less radiopaque segments 71, 73 and 75, and a plurality of discrete, outer tubular highly radiopaque segments 72, 74, and 76. The discrete outer tubular member segments are preferably manufactured from a polymeric material, such as a polyether block amide. Each segment is manufactured with selected physical properties to give a desired durometer as a measure of flexibility, which when in combination with the inner tubular member 44 and support member 62 upon assembly, give a desired flexibility of the shaft within that segment.

In a preferred embodiment, a distal catheter shaft section includes soft tip zone 76. This portion of the catheter shaft does not include a braid or support member 62 to provide an atraumatic end to the catheter shaft for navigating vasculature and engaging the coronary vessels. A polyether block amide having a 35 D durometer rating can be used in this section.

As depicted in FIG. 9, the distal end of the inner tubular member 44 terminates slightly proximal of the distal end of the soft tip zone outer tubular segment 76. This creates a super soft distal bumper zone 80 and provides a super soft interface between the catheter tip and vessel walls without increasing the chance that the tip of the catheter may prolapse. Alternatively, as depicted in FIG. 10, the inner tubular member 44 can run co-extensive with the outer tubular segments with a distal end 82 terminating at the same point as the soft tip zone outer tubular segment 76.

Outer tube segments 71, 72, 73, 74, 75, and 76 can be formed of materials of differing flexural modulus and hardness. In one embodiment, outer tubular segment 76 has a durometer of about 35 D, more proximal outer tubular segment 71 has a durometer of about 70 D, and segments 72, 73, 74, and 75 have durometer values between 35 D and 70 D, with the durometer value increasing proximally. Thus, both the flexibility and radiopacity of each segment can be varied to match the intended function and desired fluoroscopic visibility.

A preferred method of manufacturing a catheter incorporating catheter shaft portion 66 includes first providing inner tubular member 44 having support member 62 disposed over a portion thereof. A preferred method of manufacturing this subassembly is disclosed in application Ser. No. 08/800,926, filed on Feb. 13, 1997, entitled "Catheter Having an Adhesive Braid Wire Constraint and Method of Manufacture", which is incorporated herein by reference. Outer tubular segments of selected length, flexibility and radiopacity are than slidably received over the subassembly and abutted to one another as depicted in FIG. 8. A heat shrink sleeve which can be manufactured from an FEP resin is placed over the whole assembly. The assembly is then heated or baked to adhere and fuse the components of the final catheter assembly. The heat causes the materials to flow together, and the sleeve leaves a smooth outer surface. The heat shrink sleeve is then removed. This method of manufacture is preferred for the manufacture of the tubular member illustrated in FIGS. 1 through 5 as well.

The tubular segments can be formed from extruded polymeric materials having the desired flexibility, hardness, and radiopacity. In a preferred embodiment, two degrees of radiopacity are utilized in forming the tubular segments, highly radiopaque and less radiopaque. The highly radiopaque segments can be loaded close to the maximum radiopaque material loading and the less radiopaque segments can have no added radiopaque material. Heating the tube segments end to end fuses the joints, forming a smooth outer surface. The smooth surface has improved lubricity over a comparable tube having metallic bands disposed about the tube segments. The highly radiopaque segments are also unable to move over the tube.

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. A guide catheter comprising:
   an elongate, tubular, polymeric body including one or more structurally significant axial bends defined thereon and a plurality of other tubular sections;
   at least one tubular first segment forming a portion of said tubular polymeric body having a first radiopacity, said at least one tubular first segment overlaying at least a portion of a corresponding one of the structurally significant bends, and
   a plurality of tubular second segments having a second radiopacity and overlaying at least a portion of the plurality of other tubular sections of the tubular polymeric body with none of the at least one first segments positioned to significantly overlap the other tubular sections,
   wherein said first and second segments abut one another and wherein said first radiopacity is different than said second radiopacity with said radiopacity difference provided primarily by a radiopaque material incorporated into said polymeric tubular body.

2. A guide catheter as recited in claim 1 wherein said radiopaque material includes fine radiopaque particles dispersed within said polymeric material.

3. A guide catheter as recited in claim 2 wherein said first segments have an average length and said second segments have an average length and said first segment average length is greater than said second segment average length.

4. A guide catheter as recited in claim 1 wherein said first segments have an average radiopacity and said second segments have an average radiopacity, and said first radiopacity is greater than said second radiopacity.

5. A guide catheter as recited in claim 1 wherein said first segments have an average radiopacity and said second segments have an average radiopacity, and said first radiopacity is less than said second radiopacity.

6. A guide catheter as recited in claim 1 wherein said first segments and second segments include inner tubes and outer tubes, said outer tubes being disposed about said inner tubes, wherein said radiopacity is contributed primarily by radiopaque material contained within said outer tubes.

7. A guide catheter as recited in claim 6 wherein said first and second segment outer tubes have ends and said segments are joined end to end.

8. A guide catheter as recited in claim 7 wherein said end to end joining forms a substantially smooth outer tube.

9. A tubular assembly for a guide catheter comprising:
   one or more structurally significant bends and one or more other tubular sections,
   one or more highly radiopaque segments abutting one or more less radiopaque segments, said one or more highly radiopaque segments having a higher radiopacity than said less radiopaque segments,
   wherein said highly radiopaque segments are formed of polymeric material, and have said higher radiopacity resulting primarily from loading said polymeric material with a radiopaque material, and
   each of the highly radiopaque segments positioned to overlay at least part of one of the structurally significant bends, with none of the highly radiopaque segments significantly overlaying the one or more other tubular sections.

10. A tubular assembly as recited in claim 9, wherein said radiopaque material is in the form of radiopaque particles.

11. A tubular assembly as recited in claim 9, wherein said highly radiopaque segments are separated by a length that is dependent on the length between adjacent structurally significant bends.

12. A tubular assembly as recited in claim 9, wherein said tubular assembly includes an inner tube and an outer tube, wherein said outer tube is formed of said one or more highly radiopaque segments and said less radiopaque segments, wherein said outer tube segments have ends and said outer tube segments are joined end to end.

13. A tubular assembly as recited in claim 12 wherein said structurally significant bends are selected from the group consisting of secondary curve and primary curve.

14. A tubular assembly for a guide catheter comprising:
    one or more structurally significant bends and one or more other tubular sections,
    one or more highly radiopaque segments abutting one or more less radiopaque segments, said one or more highly radiopaque segments having a higher radiopacity than said less radiopaque segments,
    wherein said highly radiopaque segments are formed of polymeric material, and have said higher radiopacity resulting primarily from loading said polymeric material with a radiopaque material, and
    each of the less radiopaque segments positioned to overlay at least part of one of the structurally significant locations, with none of the less radiopaque segments significantly overlaying the one or more other tubular sections.

* * * * *